United States Patent
Gujraty et al.

(10) Patent No.: US 10,463,585 B2
(45) Date of Patent: Nov. 5, 2019

(54) COSMETIC COMPOSITIONS

(71) Applicant: The Procter & Gamble Company, Cincinnati, OH (US)

(72) Inventors: Kunal Virendra Gujraty, Singapore (SG); Shikhar Gupta, Singapore (SG); Yan Yan, Singapore (SG); Naohisa Yoshimi, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/946,745

(22) Filed: Apr. 6, 2018

(65) Prior Publication Data

US 2018/0289602 A1    Oct. 11, 2018

Related U.S. Application Data

(60) Provisional application No. 62/483,959, filed on Apr. 11, 2017.

(51) Int. Cl.

| | | |
|---|---|---|
| *A61K 8/34* | (2006.01) | |
| *A61K 8/37* | (2006.01) | |
| *A61K 8/64* | (2006.01) | |
| *A61Q 19/00* | (2006.01) | |
| *A61K 8/67* | (2006.01) | |
| *A61Q 19/08* | (2006.01) | |
| *A61K 8/60* | (2006.01) | |
| *A61Q 19/02* | (2006.01) | |
| *A61K 8/86* | (2006.01) | |

(52) U.S. Cl.
CPC .............. *A61K 8/342* (2013.01); *A61K 8/375* (2013.01); *A61K 8/60* (2013.01); *A61K 8/64* (2013.01); *A61K 8/675* (2013.01); *A61K 8/86* (2013.01); *A61Q 19/00* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 3,755,560 A | 8/1973 | Dickert et al. | |
| 4,421,769 A | 12/1983 | Dixon et al. | |
| 4,537,776 A * | 8/1985 | Cooper | A61K 9/0014 |
| | | | 514/171 |
| 9,480,634 B2 | 11/2016 | Das | |
| 9,763,864 B2 | 9/2017 | Gujraty | |
| 2003/0199584 A1 | 10/2003 | Ahluwalia | |
| 2004/0202726 A1 * | 10/2004 | DeShay | A61K 31/355 |
| | | | 424/679 |
| 2007/0148118 A1 | 6/2007 | Montanari | |
| 2009/0325885 A1 | 12/2009 | Miyata | |
| 2012/0121725 A1 | 5/2012 | Garnier | |
| 2012/0244094 A1* | 9/2012 | Farwick | A61K 8/64 |
| | | | 424/60 |
| 2016/0074312 A1 | 3/2016 | Msika | |

FOREIGN PATENT DOCUMENTS

| | | |
|---|---|---|
| EP | 2494973 A1 | 9/2012 |
| JP | 2016169163 A | 9/2016 |
| WO | WO2015010372 A1 | 1/2015 |

OTHER PUBLICATIONS

International Search Report and Written Opinion of the International Searching Authority, PCT/US2018/026363, dated Jun. 5, 2018, 15 pages.

* cited by examiner

*Primary Examiner* — Maury A Audet
(74) *Attorney, Agent, or Firm* — John G. Powell

(57) ABSTRACT

A cosmetic composition is provided, the composition comprising a safe and effective amount of a skin care active with A log P less than −2.0, a safe and effective amount of a fatty alcohol; and a safe and effective amount of a glyceryl ester. The combination of fatty alcohol and glyceryl esters surprisingly enhances penetration of skin care actives with low A log P values into skin.

5 Claims, No Drawings
Specification includes a Sequence Listing.

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Artificial sequence is synthesized

<400> SEQUENCE: 1

Pro Lys Glu Lys
1

<210> SEQ ID NO 2
<211> LENGTH: 4
<212> TYPE: PRT
<213> ORGANISM: Artificial Sequence
<220> FEATURE:
```

-continued

<223> OTHER INFORMATION: Artificial sequence is synthesized

<400> SEQUENCE: 2

Pro Gly Pro Pro
1

COSMETIC COMPOSITIONS

TECHNICAL FIELD

The present disclosure generally relates to a cosmetic composition and method of increasing penetration of skin care actives with low A log P without increasing irritation or without having a detrimental effect on the feel of a product.

BACKGROUND

Numerous water soluble skin care actives are known for providing a variety of skin care benefits. Historically, actives that are very water soluble (identified as having an A log P of less than −2.0) do not penetrate well into human skin as human skin has a more hydrophobic nature. Steps typically taken to a chassis to enhance penetration of such water-soluble skin care actives can have other negative effects on the overall composition.

For example, PKEK [SEQ ID NO: 1] has been identified as an active useful in providing skin whitening benefits. PKEK [SEQ ID NO: 1] has an A log P of −6.9. When used in a typical skin care composition—oil-in-water chassis with polymeric thickener—penetration of PKEK [SEQ ID NO: 1] is very low. To improve penetration, a new chassis was developed with high levels of emulsifiers and penetration enhancers that help maximize bioavailability. Using this chassis, an improvement in penetration was demonstrated. However, the resulting chassis was considered poor from a sensory perspective as it was overly greasy and caused irritation issues due to the high level of oil components and penetration enhancers.

Similarly, trehalose and xylitol are two known humectants that have A log Ps respectively of −3.5 and −2.5. To obtain desirable penetration levels when using these skin care actives, it is necessary to add a significant percentage of the skin care active to a composition. This results in compositions having a tacky texture/feel that is not desirable to consumers.

Over the years, efforts have been made to mitigate the negative effects caused by inclusion of these skin care actives to enable users to derive the benefits. However, there remains an opportunity to avoid some of these negative effects by simply increasing the efficiency of penetration of the skin care active present in the composition.

SUMMARY

A cosmetic composition suitable for topical application is provided. A cosmetic composition, comprising a safe and effective amount of a first skin care active having A log P less than −2.0; a safe and effective amount of a fatty alcohol; and a safe and effective amount of glyceryl ester.

The present invention further extends to a cosmetic composition comprising from about 0.001% to about 5% by weight of the composition of a skin care active having A log P of less than −2.0, wherein the skin care active is a peptide; from about 0.5% to about 15% by weight of the composition of a glyceryl ester; and from about 0.5% to about 8% by weight of the composition of a fatty alcohol.

The present invention further extends to a cosmetic composition comprising from about 0.5% to about 30% by weight of the composition of a skin care active having A log P of less than −2.0, wherein the skin care active is a humectant; from about 0.5% to about 15% by weight of the composition of a glyceryl ester; and from about 0.5% to about 8% by weight of the composition of a fatty alcohol.

DETAILED DESCRIPTION

A sequence listing that sets forth the amino acid sequence for SEQ ID NO: 1 and SEQ ID NO: 2 herein is on file an ASCII text file titled "AA1214_seq_list_ST25." This ASCII text file was created on May 31, 2019 and is 4.00 KB in size. In accordance with MPEP § 605.08 and 37 § 1.52(e), the subject matter in the ASCII text file is incorporated herein by reference.

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"A log P" as used herein, is an identification of the octanol-water partition coefficient of an active. Ghose and Crippen used this atom-based method to calculate the octanol-water partition coefficient (log P), and the molar refractivity (MR) for incoming molecules. Log P provides a measure of the hydrophobicity of the molecule, while MR contains information about molecular volume and polarizability. A log P is calculated herein using Pipeline Pilot software (Biovia™) ver 9.2.

"Cosmetic composition" as used herein, means compositions suitable for topical application on mammalian keratinous tissue.

"Derivatives" as used herein, includes but is not limited to, amide, ether, ester, amino, carboxyl, acetyl, aldehyde, ketone, and/or alcohol derivatives of a given compound.

"Diluent" as used herein, includes a material in which compounds (e.g. a skin care active or skin lightening agent) can be dispersed, dissolved, or otherwise incorporated.

"Keratinous tissue" as used herein, refers to keratin-containing layers disposed as the outermost protective covering of mammals which includes, but is not limited to, skin, hair, nails, cuticles, etc.

"Safe and effective amount" as used herein, means an amount sufficient to induce one or more biological effects, but low enough to avoid serious side effect, (e.g. undue toxicity or allergic reaction).

"Skin care actives" as used herein, means compounds that, when applied to the skin, provide a benefit or improvement to the skin. It is to be understood that skin care actives are useful not only for application to skin, but also to hair, nails and other mammalian keratinous tissue.

It has been discovered that the combination of fatty alcohols and glyceryl esters together with a skin care active having a low A log P value results in enhanced penetration of the skin care active into skin. For example, it has been shown that incorporating actives with low A log P (peptides, sugars, sugar alcohols, etc.) in a chassis with fatty alcohols and glyceryl esters improves penetration of these actives into skin vs a standard oil-in-water based chassis with polymeric thickeners. This increase in penetration comes without compromising the sensory feel of the skin care composition or without increasing irritation caused by the skin care active. In fact, without being bound by theory, it is thought that the combination of the fatty alcohols and glyceryl esters forms a lamellar gel network that provides a pleasant sensory experience to users while additionally providing an efficient vehicle to deliver skin care actives with low A log P into skin.

Cosmetic Compositions

A cosmetic composition of the present invention may be applied to mammalian keratinous tissue, in particular to human skin. The cosmetic compositions may take various forms. For example, some non-limiting examples of forms include solutions, suspensions, lotions, creams, gels, toners, sticks, pencils, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, cosmetics (e.g. foundations, eye liners, eye shadows), and the like.

The cosmetic composition includes at least a first skin care active having low A log P, where "low" is equated to less than −2.0, less than −3.0 or less than −4.0. In embodiments, the skin care active may be a peptide or humectant having low A log P, although it will be appreciated that there may be other skin care actives with low A log P that could be used. Alternatively, more than one skin care active having low A log P may be included in the composition and/or a first skin care active with low A log P may be incorporated together with other skin care actives that have higher A log P values (e.g., a vitamin B compound such as niacinamide).

In an embodiment, the first skin care active is a peptide, such as PKEK [SEQ ID NO: 1] PGPP [SEQ ID NO: 2] or RGS (AT Peptide). A "peptide" is a compound that includes an uninterrupted sequence of two or more amino acids within its structure. The term "amino acid" as used herein includes and encompasses all of the naturally occurring amino acids, both in the D- or L-configuration if optically active, and the known non-native, synthetic, and modified amino acids, such as homocysteine, ornithine, norleucine and p-valine. Derivatives are also considered to be encompassed by the term "peptides" in accordance with the present invention.

As an example, AT Peptide (from Ashland™) has been shown to enhance cell energy rebound, boost cells' metabolism and provide cutaneous cells with an energy supply that improves fundamental physiological processes such as epidermal differentiation, thereby helping the skin to recover from physiological changes or environmental stresses.

Tetrapeptide PKEK [SEQ ID NO: 1] is known for treatment of skin pigmentation by interfering with the keratinocyte to melanocyte signaling processes. This has been shown in vivo to reduce tyrosinase expression.

PGPP [SEQ ID NO: 2] is known for high efficacy in wound healing and fibronectin induction in skin—all endpoints relevant for anti-ageing.

PKEK (A log P −6.9), PGPP [SEQ ID NO: 2] (A log P −4.0) and AT Peptide (A log P −6.1) typically do not penetrate well into skin since they are very water soluble and skin is typically hydrophobic in nature.

Simply increasing the percentage of these peptides in a composition as a means to increase the amount that penetrates into skin may lead to increased irritation to skin and is a cost-ineffective proposition. In embodiments, the cosmetic composition includes a safe and effective amount of one or a combination of PKEK [SEQ ID NO: 1], PGPP [SEQ ID NO: 2], RGS and ATPeptide, preferably from 0.001%, 0.004% or 0.01% to 1%, 2.5% or 5% by weight of the total composition.

In alternative embodiments, the skin care active having low A log P may be a humectant (for example, a sugar or polyol/sugar alcohol). Sugars and sugar alcohols are small, polar molecules with affinity to H-bond with water and accordingly bind to water molecules. As with highly polar peptides, sugars/sugar alcohols like xylitol (A log P of −2.4) and trehalose (A log P of −3.4) typically do not penetrate well into skin. Thus, to achieve a desirable benefit from such humectants, it is typically necessary to increase the percentage of the humectant in the composition. While this may not lead to problems relating to irritation of skin, the sensory experience of a composition containing high levels of humectant will be significantly compromised. In this respect, increasing the levels of humectant may lead to a tacky and unpleasant composition.

In embodiments, the cosmetic composition includes a safe and effective amount of a humectant having low A log P, such as xylitol or trehalose, preferably from 0.5%, 2.5%, 5% or 7.5% to 10%, 15%, 20% or 30% by weight of the composition.

In alternative embodiments, the cosmetic composition includes a combination of different skin care actives having low A log P, for example, the composition may include PKEK [SEQ ID NO: 1] and one or both of trehalose and xylitol.

The cosmetic composition further comprises a safe and effective amount of one or more fatty alcohols. Fatty alcohols in the present invention assist to stabilize the emulsion and provide cosmetically acceptable viscosity for the composition. Fatty alcohols typically contain fatty alcohol moieties with chain lengths of from $C_8$ to $C_{22}$. The fatty alcohol material may also contain relatively pure amounts of one chain length fatty alcohol moiety. Suitable fatty alcohols from which fatty alcohol/surfactant base mixtures are derived may include pelargonic, lauric, myristic, palmitic, stearic, isostearic, oleic, linoleic, ricinoleic, arachidic, behanic and erucic alcohols. The cosmetic composition includes a safe and effective amount of fatty alcohol, preferably between 0.5%, 0.75% or 1% to 4%, 6% or 8% by weight of the total composition. In a preferred embodiment, the fatty alcohol used is selected from the group consisting of cetyl, stearyl or behenyl alcohols The cosmetic composition further comprises a safe and effective amount of one or more glyceryl esters. Examples of glyceryl esters include, but are not limited to: glyceryl stearate, glyceryl oleate, glyceryl isostearate, glyceryl noerucate, glyceryl hydroxystearate and glyceryl linoleate. The cosmetic composition includes a safe and effective amount of glyceryl ester, preferably between 0.5%. 0.75%, 1% or 1.5% and 8%, 10%, 12% or 15% by weight of the total composition.

In embodiments, the composition further includes polyoxyethylene esters with fatty acid. Examples of polyoxyethylene esters with fatty acid include, but are not limited to: PEG-100 stearate, PEG-200 stearate, PEG-20 stearate, PEG-40 stearate and PEG-20 myristate.

Where the composition includes polyoxyethylene esters with fatty acid, the amount of glyceryl ester may be reduced. Thus, in embodiments, there may be a total amount of glyceryl ester and polyoxyethylene ester of between 0.5%, 0.75%, 1% or 1.5% to 8%, 10%, 12% or 15% by weight of the total composition, where the ratio of glyceryl ester to polyoxyethylene ester is between 0.1:0.9 to 1:0, 1:3 to 3:1, 1:2 to 2:1 or 1:1.

Other Ingredients

The cosmetic composition may include one or more skin care actives, for example vitamin B3 actives such as niacinamide. The topical application of niacinamide may be associated with a variety of cosmetic skin care benefits. These may include: i) normalization of age associated depletions of nicotinamide coenzymes in skin, ii) up-regulation of epidermal ceramide synthesis with concurrent epidermal barrier benefits, iii) protection against damage produced by UV irradiation, iv) inhibition of the transfer of melanosomes from melanocytes to keratinocytes (thereby providing a potential skin tone benefit), and reduction in sebaceous lipogenesis. Thus in certain instances, it may be desirable to include niacinamide in the cosmetic composition in order to improve the appearance of aging/photo-damaged skin.

The cosmetic compositions may also comprise a dermatologically acceptable carrier (which may also be referred to as a "carrier") within which the humectant, chaotropic agent and lipid bilayer structurant are incorporated to enable the compounds and optional other ingredients to be delivered to the skin. The carrier may contain one or more dermatologically acceptable solid, semi-solid or liquid fillers, diluents, solvents, extenders components, materials and the like. The carrier may be solid, semi-solid or liquid. The carrier may be provided in a wide variety of forms. Some non-limiting examples include simple solutions, (aqueous or oil based), emulsions, mousses (aerosol, non-aerosol), and solid forms (e.g., gels, sticks, flowable solids, amorphous materials).

The carriers may contain one or more dermatologically acceptable, hydrophilic diluents. Hydrophilic diluents include water, organic hydrophilic diluents such as lower monovalent alcohols (e.g., C1-C4) and low molecular weight glycols and polyols, including, but not limited to, propylene glycol, butylenes glycol, pentylene glycol, hexylene glycol, octylene glycol, polyethylene glycol (e.g., molecular weight 200-600 g/mole), polypropylene glycol (e.g., molecular weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Carriers may also be in the form of an emulsion, such as oil-in-water emulsions, water-in-oil emulsions, and water-in-silicone emulsions. An emulsion may generally be classified as having a continuous aqueous phase (e.g., oil-in-water and water-in-oil-in-water) or a continuous oil phase (e.g., water-in-oil and oil-in-water-in-oil). The oil phase may comprise silicone oils, non-silicone oils such as hydrocarbon oils, esters, ethers, and the like, and mixtures thereof. The aqueous phase may comprise water, such as a solution as described above. However, in other embodiments, the aqueous phase may comprise components other than water, including but not limited to water-soluble moisturizing agents, conditioning agents, anti-microbials, chelating agents, and/or other water-soluble skin care actives. Emulsions may also contain from about 1% to about 10% or from about 2% to about 5%, of an emulsifier, based on the weight of the carrier. Emulsifiers may be nonionic, anionic or cationic. Some suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986).

A wide variety of optional components/ingredients may be included in the cosmetic compositions. For example, the cosmetic compositions may include absorbents, abrasives, anticaking agents, antifoaming agents, antimicrobial agents, binders, biological additives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, oil/sebum control agents, sweat control agents, sequestrants, anti-acne agents, anti-inflammatory agents, anti-androgens, depilation agents, desquamation agents/exfoliants, organic hydroxy acids, vitamins and derivatives thereof, and natural extracts. Such other materials are known in the art. Nonexclusive examples of such materials are described in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker, Inc.; in The Chemistry and Manufacture of Cosmetics, 2nd. Ed., deNavarre (Van Nostrand 1962-1965); and in The Handbook of Cosmetic Science and Technology, 1st Ed. Knowlton & Pearce (Elsevier 1993).

Various cosmetic treatments may be employed. Skin surfaces of the most concern tend to be those not typically covered by clothing such as facial skin surfaces, hand and arm skin surfaces, foot and leg skin surfaces, and neck and chest skin surfaces. In particular, facial skin surfaces, including the forehead, perioral, chin, periorbital, nose, and/or cheek skin surfaces, may be treated with the cosmetic compositions described herein.

The treatment method may include applying the cosmetic composition to a previously identified area of skin in need of treatment, or an area where one seeks to prevent, treat or reduce the appearance of age spots and/or improve skin tone evenness. Many regimens exist for the application of the cosmetic composition. The cosmetic composition may be applied at least once a day, twice a day, or on a more frequent daily basis, during a treatment period. When applied twice daily, the first and second applications are separated by at least 1 to 12 hours. Typically, the cosmetic composition may be applied in the morning and/or in the evening before bed.

The treatment period is ideally of sufficient time to provide an improvement in the appearance of the age spots or skin tone evenness. The treatment period may be at least 1 week, and in some embodiments the treatment period may last about 4 weeks, 8 weeks, or 12 weeks. In certain embodiments, the treatment period will extend over multiple months (i.e., 3-12 months) or multiple years. In one embodiment the cosmetic composition is applied at least once a day during a treatment period of at least 4 weeks, 8 weeks, or 12 weeks. In one embodiment the cosmetic composition is applied twice a day during a treatment period of at least 4 weeks, 8 weeks, or 12 weeks.

A method of using a cosmetic composition may comprise applying the cosmetic composition of the present invention to a facial skin surface in need of treatment. Furthermore, a method of enhancing skin hydration may comprise topically applying the cosmetic composition of the present invention to a skin surface.

Examples

The following examples are given solely for the purpose of illustration and are not to be construed as limiting the invention, as many variations thereof are possible. All measurements below are % by weight of the total composition.

TABLE 1

|  | Benchmark | Example 1 | Example 2 | Example 3 | Example 4 | Example 5 |
|---|---|---|---|---|---|---|
| Glyceryl Stearate | 0% | 2% | 2% | 2% | 2% | 2% |
| PEG-100 Stearate | 0.1% | 2.1% | 2.1% | 2.1% | 2.1% | 2.1% |
| Fatty Alcohol | 0.25% | 2.25% | 2.25% | 2.25% | 1.25% | 3.25% |
| Cetearyl Glucoside | 0.25% | 0.25% | 0.25% | 0.25% | 0.25% | 0.25% |
| Other Oil/Wax component | 4.83% | 5.83% | 5.83% | 4.83% | 5.83% | 5.83% |
| Preservative | 1.275% | 1.275% | 1.275% | 1.275% | 1.275% | 1.275% |
| Glycerin | 5% | 5% | 0% | 5% | 5% | 5% |
| Sepigel 305 | 1% | 0% | 0% | 0% | 0% | 0% |
| Niacinamide | 5% | 5% | 5% | 5% | 5% | 5% |
| PKEK [SEQ ID NO: 1] | 0.004% | 0.004% | 0.004% | 0.004% | 0.004% | 0.004% |
| Water | q.s. | q.s. | q.s. | q.s. | q.s. | q.s. |

|  | Example 6 | Example 7 | Example 8 | Example 9 |
|---|---|---|---|---|
| Glyceryl Stearate | 1% | 4% | 1.5% | 1% |
| PEG-100 Stearate | 1.1% | 4.1% | 1.6% | 1.1% |
| Fatty Alcohol | 1.25% | 4.25% | 2.25% | 2.25% |
| Cetearyl Glucoside | 0.25% | 0.25% | 0.25% | 0.25% |
| Other Oil/Wax component | 5.33% | 6.83% | 6.33% | 6.83% |
| Preservative | 1.275% | 1.275% | 1.275% | 1.275% |
| Glycerin | 5% | 5% | 5% | 5% |
| Sepigel 305 | 0% | 0% | 0% | 0% |
| Niacinamide | 5% | 5% | 5% | 5% |
| PKEK [SEQ ID NO: 1] | 0.004% | 0.004% | 0.004% | 0.004% |
| Water | q.s. | q.s. | q.s. | q.s. |

Note:
Sepigel 305 ™ is a mixture of Polyacrylamide, C13-14 Isoparaffin and Laureth-7, supplied from Seppic ™.

In vitro skin penetration studies were conducted to characterize the impact of combining glyceryl esters and fatty alcohol upon in vitro skin penetration of radiolabeled PKEK [SEQ ID NO: 1] in several cosmetic compositions. Table 1 provides a general description of the cosmetic composition that were tested.

cals (St. Louis, Mo.). For all studies, split-thickness human cadaver skin was maintained at −70° C. until thawed at ambient conditions, rinsed with distilled water, cut into appropriately sized sections, and mounted in standard Franz-type diffusion cells (0.79 cm$^2$) which were placed in heating/stirring blocks thermostatted to maintain a skin surface temperature of about 34° C. The receptors [~5 mL] were filled with a solution of 1% polysorbate 20 (VWR International, West Chester, Pa.) in Dulbecco's Phosphate Buffered

TABLE 2

|  | Benchmark | Example 1 | Example 2 | Example 3 | Example 4 | Example 5 | Example 6 | Example 7 | Example 8 | Example 9 |
|---|---|---|---|---|---|---|---|---|---|---|
| Skin Penetration (μg/cM2) | 5.19 | 9.43 | 11.10 | 12.01 | 9.08 | 13.46 | 11.52 | 29.24 | 22.12 | 24.59 |
| Total Penetration (μg/cM2) | 11.79 | 16.48 | 19.89 | 23.54 | 20.74 | 25.32 | 21.07 | 39.44 | 32.54 | 33.94 |

Note 1:
Each number is average of 6 data points
Note 2:
Skin Penetration = PKEK [SEQ ID NO: 1] in Epidermis + PKEK [SEQ ID NO: 1] in Dermis
Note 3:
Total Penetration = PKEK [SEQ ID NO: 1] in skin (= Epidermis + Dermis) + PKEK [SEQ ID NO: 1] in Receptor
Note 4:
Each example combining glyceryl esters with fatty alcohol shows a statistically significant ($p < 0.05$) increase in penetration for skin and total penetration vs the benchmark data.

Test Method:
Split thickness cadaver skin was obtained from AlloSource (Englewood, Colo.). Tritiated water was from PerkinElmer (Boston, Mass.) while radiolabeled PKEK [SEQ ID NO: 1] was obtained from American Radiochemi- Saline [PBS] (Sigma-Aldrich, Inc., St. Louis, Mo.) with agitation provided by magnetic stir bars, and the skin allowed to equilibrate for at least two hours.

Six cells were randomized to each treatment in a given study based upon $^3$H$_2$O flux through the mounted skin.[16] 150

μL $^3H_2O$ were applied to the mounted cadaver skin for five minutes and any non-absorbed liquid subsequently removed with a cotton swab. After a minimum of one hour to achieve equilibrium, the receptor contents were collected. LCS (14 mL) was added to the contents of each receptor and also to triplicate 150 μL aliquots of $^3H_2O$. The LSC solutions and appropriate blanks were assayed for total radiolabel by liquid scintillation counting for one minute using a pre-set quench curve. Blank corrected DPM (disintegrations per minute) in each receptor was converted to μL $^3H_2O$ using the mean of the blank corrected DPM of the 150 μL aliquots of $^3H_2O$, and water flux for each cell was calculated as the quotient of the $^3H_2O$ volume detected in the receptor and the available skin surface area. Fresh receptor fluid was then added to the receptor portions of the Franz cells and the cells allowed to further equilibrate overnight.

Following the overnight equilibration period, the receptor compartments were filled with fresh media. Except as noted below, approximately 5 μL of product with radiotracer were applied to the individual cells using a positive displacement pipette. The receptor solution was collected and replaced at 2 and 4 hr with a final collection at 6 hr. At the end of the test time (s), each skin sample was wiped two times with Whatman filter paper soaked with PBS containing 1% polysorbate 20 and once with filter paper soaked with 70%/30% ethanol/distilled water to remove unabsorbed (residual) product. The epidermis (including stratum corneum) was separated from the residual dermis by dissection.

Disintegrations-per-minute (DPM) obtained for the various components of each cell (all receptor collections, filter paper wipes, epidermis, and dermis) were blank corrected and summed to obtain a total recovered radiolabel value for a given cell. This value was then compared with the specific radiolabel activity of the product (DPM/theoretical dose) to estimate the percent recovery of the theoretical dose.

The blank corrected DPM of each compartment were then normalized to the total recovered radiolabel value to obtain a "percent recovered radiolabel" parameter for each component. This compensates for variations in the amount of product dosed due to its viscosity and improves study precision.

Cumulative receptor amounts were calculated as the sums of the various receptor collections to a given time point. A total skin value was calculated as the sum of the epidermis and dermis fractions, and a total permeated value calculated as the sum of total skin and total cumulative receptor.

For those studies which incorporated test products with varying concentrations of the permeant being investigated (e.g. PKEK [SEQ ID NO: 1]), the percent recovered values were subsequently converted to "fraction radiolabel recovered" by dividing by 100, and then to amount (μg-equivalents (μg-eq) permeant by multiplying by the target dose (5 mg) and fraction permeant in the test product.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition, comprising:
 a) 1% to 1.5% glyceryl stearate;
 1.1% to 1.6% PEG-100 stearate;
 2.25% of a fatty alcohol selected from the group consisting of cetyl, stearyl, and behenyl alcohol;
 about 0.25% cetearyl glucoside;
 about 4.8% to about 6.8% of an oil or wax component;
 about 1% of a preservative;
 0% to 5% glycerin;
 about 5% niacinamide;
 about 0.004% PKEK [SEQ ID NO:1]; and
 water q.s.

2. The cosmetic composition of claim 1, wherein the cosmetic composition further comprises an effective amount of polyoxyethylene ester.

3. The cosmetic composition of claim 2, wherein the total amount of glyceryl ester and polyoxyethylene ester is from 0.5% to 15% by weight of the total composition and the ratio of glyceryl ester to polyoxyethylene ester is from 0.1:0.9 to 1:1.

4. The cosmetic composition of claim 1, wherein the composition further comprises at least one additional skin care active, wherein the additional skin care active has A log P of more or less than −2.0.

5. The cosmetic composition of claim 4, wherein the additional skin care active is a humectant selected from the group consisting of xylitol and trehalose; or a peptide selected from the group consisting of PGPP [SEQ ID NO: 2] and RGS.

* * * * *